(12) United States Patent
Robinson

(10) Patent No.: US 6,636,759 B2
(45) Date of Patent: Oct. 21, 2003

(54) APPARATUS AND METHOD FOR DETERMINATION OF THE ADEQUACY OF DIALYSIS BY NON-INVASIVE NEAR-INFRARED SPECTROSCOPY

(75) Inventor: Mark Ries Robinson, Albuquerque, NM (US)

(73) Assignee: Inlight Solutions, Inc., Albuquerque, NM (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/819,239

(22) Filed: Mar. 28, 2001

(65) Prior Publication Data

US 2001/0018560 A1 Aug. 30, 2001

Related U.S. Application Data

(63) Continuation of application No. 09/182,340, filed on Oct. 29, 1998, now Pat. No. 6,212,424.

(51) Int. Cl.$^7$ .................................................. A61B 5/00
(52) U.S. Cl. ........................................ 600/475; 600/310
(58) Field of Search ................................ 600/473, 475, 600/476, 310, 322; 604/4, 5; 356/342, 433

(56) References Cited

U.S. PATENT DOCUMENTS

| | | | |
|---|---|---|---|
| 3,508,830 A | 4/1970 | Hopkins et al. ............ 356/103 |
| 3,992,158 A | 11/1976 | Przybylowicz et al. ....... 23/253 |
| 4,427,889 A | 1/1984 | Muller ........................ 250/339 |
| 4,655,225 A | 4/1987 | Dahne et al. ................ 128/633 |
| 4,661,706 A | 4/1987 | Messerschmidt et al. ... 250/341 |
| 4,853,542 A | 8/1989 | Milosevic et al. .......... 250/353 |
| 4,882,492 A | 11/1989 | Schlager .................... 250/346 |
| 4,975,581 A | 12/1990 | Robinson et al. ........... 250/339 |
| 5,015,100 A | 5/1991 | Doyle ........................ 356/445 |
| 5,019,715 A | 5/1991 | Sting et al. ................. 250/571 |
| 5,028,787 A | 7/1991 | Rosenthal et al. .......... 250/341 |
| 5,051,602 A | 9/1991 | Sting et al. ................. 250/571 |
| 5,070,874 A | 12/1991 | Barnes et al. ............... 128/633 |
| 5,158,082 A | 10/1992 | Jones ......................... 128/633 |

(List continued on next page.)

FOREIGN PATENT DOCUMENTS

| | | |
|---|---|---|
| WO | WO 92/17765 | 10/1992 |
| WO | WO 93/07801 | 4/1993 |
| WO | WO 95/04266 | 2/1995 |
| WO | WO 98/19592 | 5/1998 |

OTHER PUBLICATIONS

Berkoben et al., "Vascular Access for Hemodialysis", *Clinical Dialysis*, published on or before Oct. 30, 1997, 20 pages.

(List continued on next page.)

*Primary Examiner*—Shawna J Shaw
(74) *Attorney, Agent, or Firm*—Crompton, Seager & Tufte, LLC.; David Crompton

(57) ABSTRACT

Methods and apparatus for non-invasive tissue urea concentrations during or subsequent to hemodialysis using near-infrared spectroscopy are discussed. Near-infrared tissue spectra can be obtained by projecting near-infrared radiation into skin on the underside of human forearms and capturing the light reflected back and out through the tissue. An index matching medium is used to couple the tissue to the analyzer. The tissue spectrum collected preferably includes primarily diffuse reflected light reflected from the inner dermis. Multiple tissue spectra of known urea concentration are used to build a model from which the urea concentration of an unknown sample can be devised. The model is based on a partial least squares algorithm applied to multiple tissue scans and concomitant blood sample urea measurements. This model is then applied to an unknown tissue spectra.

7 Claims, 8 Drawing Sheets

U.S. PATENT DOCUMENTS

| | | | |
|---|---|---|---|
| 5,179,951 A | 1/1993 | Knudson | 128/633 |
| 5,222,496 A | 6/1993 | Clarke et al. | 128/633 |
| 5,230,702 A | 7/1993 | Lindsay et al. | 604/4 |
| 5,237,178 A | 8/1993 | Rosenthal et al. | 250/341 |
| 5,299,570 A | 4/1994 | Hatschek | 128/633 |
| 5,321,265 A | 6/1994 | Block | 250/343 |
| 5,331,958 A | 7/1994 | Oppenheimer | 128/633 |
| 5,348,003 A | 9/1994 | Caro | 128/633 |
| 5,351,686 A | 10/1994 | Steuer et al. | 128/633 |
| 5,355,880 A | 10/1994 | Thomas et al. | 128/633 |
| 5,361,758 A * | 11/1994 | Hall et al. | 600/322 |
| 5,366,903 A | 11/1994 | Lundsgaard et al. | 436/165 |
| 5,372,135 A | 12/1994 | Mendelson et al. | 128/633 |
| 5,379,764 A | 1/1995 | Barnes et al. | 128/633 |
| 5,402,778 A | 4/1995 | Chance | 128/633 |
| 5,405,315 A | 4/1995 | Khuri et al. | 604/4 |
| 5,452,723 A | 9/1995 | Wu et al. | 128/664 |
| 5,505,726 A | 4/1996 | Meserol | 606/9 |
| 5,507,723 A | 4/1996 | Kashaviah | 604/5 |
| 5,515,847 A | 5/1996 | Braig et al. | 128/633 |
| 5,518,623 A | 5/1996 | Keshaviah et al. | 210/646 |
| 5,523,054 A | 6/1996 | Switalski et al. | 422/58 |
| 5,533,509 A | 7/1996 | Koashi et al. | 128/633 |
| 5,601,080 A | 2/1997 | Oppenheimer | 128/633 |
| 5,636,633 A | 6/1997 | Messerschmidt et al. | 128/633 |
| 5,655,530 A | 8/1997 | Messerschmidt | 128/633 |
| 5,681,273 A | 10/1997 | Brown | 604/6 |
| 5,698,083 A | 12/1997 | Glass | 204/403 |
| 5,725,773 A | 3/1998 | Polaschegg | 210/636 |
| 5,817,007 A * | 10/1998 | Fodgaard et al. | 600/322 |
| 5,818,048 A | 10/1998 | Sodickson et al. | 250/343 |
| 5,823,951 A | 10/1998 | Messerschmidt | 600/322 |
| 5,935,062 A | 8/1999 | Messerschmidt et al. | 600/322 |
| 6,021,339 A | 2/2000 | Saito et al. | 600/345 |
| 6,044,285 A * | 3/2000 | Chaiken et al. | 600/316 |
| 6,151,522 A * | 11/2000 | Alfano et al. | 600/473 |
| 6,152,876 A | 11/2000 | Robinson et al. | 600/322 |
| 6,212,424 B1 | 4/2001 | Robinson | 600/475 |
| 6,236,047 B1 * | 5/2001 | Malin et al. | 250/339.12 |
| 6,258,027 B1 * | 7/2001 | Sternby | 600/366 |

OTHER PUBLICATIONS

Bleyer et al., "The costs of Hospitalizations Due to Hemodialysis Access Management", *Nephrology News & Issues*, Jan. 1995, pp. 19–47.

Daugirdas et al., "Comparison of Methods to Predict the Equilibrated Kt/V (eKt/V) in the Hemo Study", National Institutes of Health, NIDDK, Bethlehem, MD, Aug. 20, 1996.

Depner et al., "Clinical Measurement of Blood Flow in Hemodialysis Access Fistulae and Grafts by Ultrasound Dilution", from the Department of Nephrology, University of California, published on or before Oct. 30, 1997, pp. M745–M749.

Depner et al., "Hemodialysis Access Recirculation Measured by Ultrasound Dilution", from the Department of Nephrology, University of California, published on or before Oct. 30, 1997, pp. M749–M753.

Hakim et al., "Effects of Dose of Dialysis on Morbidity and Mortality", *American Journal of Kidney Diseases*, vol. 23, No. 5, May 1994, pp. 661–669.

Hall, Jeffrey W. et al., "Near–Infrared Spectroscopic Determination of Serum Total Proteins, Albumin, Globulins, and Urea," *Clinical Biochemistry*, vol. 26, Dec. 1993, pp. 483–490.

Jacobs et al., "A Disposable urea Sensor for Continuous Monitoring of Hemodialysis Efficiency", *ASAIO Journal*, 1993, pp. M353–M358.

Keshaviah et al., "On–line monitoring of the delivery of the hemodialysis prescription", *Pediatric Nephrology*, vol. 9, 1995, pp. S2–S8.

Krivitski, "Theory and Validation of Access Flow Measurement by Dilution Technique During Hemodialysis", *Kidney International*, vol. 48, 1995, pp. 244–250.

Marbach, "Measurement Techniques for IR Spectroscopic Blood Glucose Determination", 1993.

Ronco et al., "On–line urea monitoring: a further step towards adequate dialysis prescription and delivery", *Int'l Journal of Artificial Organs*vol. 18, No. 9, 1995, pp. 534–543.

Shaw, R. Anthony et al., Quantitaion of Protein, Creatinine, and Urea in Urine by Near–Infrared Spectroscopy, *Clinical Biochemistry*, vol. 29, Feb. 1996, pp. 11–19.

Sherman, "Recirculation in the Hemodialysis Access", *Principles and Practice of Dialysis*, published on or before Oct. 30, 1997, 9 pages.

Sherman, "The Measurement of Dialysis Access Recirculation", *American Journal of Kidney Diseases*, vol. 22, No. 4, Oct. 1993, pp. 616–621.

Steuer et al., "A New Optical Technique for Monitoring Hematocrit and Circulating Blood Volume: Its Application in Renal Dialysis", *Dialysis & Transportation*, vol. 22, No. 5, May 1993, 5 pages.

Brochure entitled "Determination of Delivered Therapy Through Measurement of Effective Clearance", Fresenius USA, Dec. 1994, 1 page.

Brochure entitled "Improve the Clinical Outcome of Every Patient", In Line Diagnostics, published on or before Oct. 30, 1997, 2 pages.

* cited by examiner

APPARATUS AND METHOD FOR DETERMINATION OF THE ADEQUACY OF DIALYSIS BY NON-INVASIVE NEAR-INFRARED SPECTROSCOPY

CROSS REFERENCE TO RELATED PATENTS AND PENDING APPLICATIONS

This application is a continuation of pending U.S. patent application Ser. No. 09/182,340. Filed on Oct. 29, 1998 now U.S. Pat. No. 6,212,424 issued Apr. 3, 2001. The present application is related to U.S. patent application Ser. No. 09/174,812, filed Oct. 19, 1998 now U.S. Pat. No. 6,152,876 issued Nov. 28, 2000, entitled "Method for Non-Invasive Analyte Measurement with Improved Optical Interface"; U.S. patent application Ser. No. 08/871,366, filed Jun. 9, 1997 now U.S. Pat. No. 5,935,062 issued Aug. 10, 1999 entitled "Diffuse Reflectance Monitoring Apparatus"; and U.S. patent application Ser. No. 08/961,323, filed Oct. 30, 1997 now abandoned, entitled "Dialysis Monitoring Method and Apparatus", all of which are assigned to the same assignee as the present application.

TECHNICAL FIELD

The present invention relates generally to methods and systems for determining the adequacy of treatment during hemodialysis of a patient utilizing a non-invasive near-infrared tissue analysis. More specifically, the invention relates to direct measurement of urea concentrations in tissue of patients undergoing dialysis with light diffusely reflected by skin in conjunction with a spectrographic model, which relates urea concentration to a diffusely reflected light spectrum.

BACKGROUND OF THE INVENTION

Measurement of the efficacy of hemodialysis treatments is currently time consuming, inaccurate and expensive. Approximately 260,000 Americans suffer from end-stage renal disease (ESRD). Fifty-nine percent are treated by thrice-weekly maintenance hemodialysis sessions designed to clear the products of metabolism that are normally excreted by the kidneys in the urine. Since the failure to adequately dialyze a patient has been shown to increase mortality and morbidity and since the process of dialyzing an ESRD patient is complex and variable in terms of the efficiency of the treatment, a number of methods have been developed to quantify the effectiveness of the treatment. The technique used in the overwhelming majority of dialysis centers is based on pre- and post-dialysis measurements of blood urea nitrogen concentrations. Urea, a low-molecular weight molecule, is a product of protein metabolism that is normally cleared from the body by the kidneys. Because it is also cleared from the blood by the dialysis process and easily measured in blood, its disappearance from the blood during hemodialysis is a measure of the efficacy or adequacy of that particular treatment session. The process of removal of toxins from the body by hemodialysis is best represented as a logarithmic function. As such, the coefficient of the natural logarithm termed KT/Vd, which is calculated from pre- and post-dialysis measurements of blood urea concentrations, can be used as a single descriptor of dialysis adequacy.

The importance of adequate duration or dose of hemodialysis has been underscored recently by the observation that the adjusted mortality of patients with renal disease in the United States exceeds that of several other countries, despite a longer life expectancy of the general population of the United States. A number of studies have documented the failure to deliver an adequate dose of hemodialysis to many Americans. The failure of delivery of adequate hemodialysis doses in the United States is a result of many factors. Time and financial pressures contribute to the problem. Because the metabolic toxins are removed from the blood, which makes up only a fraction of the total volume of the body in which the toxins are distributed, there are delays as the solutes redistribute and equilibrate after dialysis. Thus, measurement of KT/Vd is highly dependent on the time of the urea measurements and the relative size of the compartments such as blood water, interstitial water and intracellular water, all of which harbor urea and other contaminants. These compartments vary in size from patient to patient, and within a patient depending upon present physiologic state. The best measure of the post-dialysis urea is made at least 15 minutes after hemodialysis, but for some patients it may require 50 to 60 minutes to reach equilibrium. There is no accurate way to predict which patients will have a significant blood urea increase following hemodialysis at any given treatment time. Given the time constraints on out-patient hemodialysis centers that commonly are able to dialyze no more than two patients per day on a single machine, one in the morning and one in the afternoon, the need to obtain post-dialysis blood urea concentrations 30 to 60 minutes after dialysis is impractical at best. Finally, the late blood measurement requires an additional venipuncture of the patient who is disconnected from the dialysis machine minutes after cessation of circulation through the machine.

Urea testing is a capital burden on the dialysis centers that provide dialysis to ESRD patients under a capitated reimbursement basis. The blood drawing process is labor intensive and exposes the nursing staff to blood borne pathogens. The samples must then be transported to a laboratory for analysis, incurring another charge and a delay in reported values. Currently, the accepted "standard of care" given financial constraints is that KT/Vd be measured once per month, that is, once during every 12 dialysis sessions. In summary, hemodialysis is "under-delivered" in the United States. Financial and time constraints result in failure to recognize such inadequacy given the infrequent collection of blood for urea samples and calculation of KT/Vd, as well as poor modeling due to variability of the rebound effect and early post dialysis blood collection.

As noted above, monitoring the adequacy of hemodialysis, as defined by the National Kidney Foundation (NKF)—"1997 DOQI Clinical Practice Guidelines for Hemodialysis Adequacy", and the Renal Physicians Associations (RPA) "1993 Clinical Practice Guidelines on Adequacy of Hemodialysis", entail measuring blood urea nitrogen (BUN) pre- and post-dialysis once per month in order to calculate the so-called single pool KT/Vd value with K=dialyzer clearance, T=time of dialysis, and V=volume of distribution of urea. KT/Vd is then calculated from pre- and post-dialysis BUN concentrations by the following formula:

$$KT/V = -Ln(Ct/Co - 0.008t - UF/W)$$

Where Ct is the post-dialysis urea level and Co is the pre-dialysis urea level; t is the time; UF is the ultrafiltrate removed; and W is the post-dialysis weight.

The equation is most representative of the true dialysis dose if the post session BUN blood sample is drawn after the blood urea has equilibrated with the interstitial and intracellular urea. Release of sequestered urea from the intracellular space to the extracellular space continues for 30 to 60 minutes after completion of a dialysis session. This equilibration is due to the removal of urea from the blood by the dialyzer at a rate that exceeds the rate of diffusion from the intracellular to the extracellular compartment. Delays of equilibrium are also caused by the so-called "flow-volume disequilibrium". Seventy percent of the total body water is contained in organs that receive only 20% of the cardiac output. Relatively poorly perfused tissues such as skin, muscle, and bone are cleared of urea less efficiently than highly vascularized organs such as the liver or lungs. The consequence of this compartmentalization of urea is an increase in the BUN concentration over the 60 minutes after the completion of hemodialysis.

The magnitude of the urea rebound varies greatly among dialysis patients. The average increase of urea concentration in the 30 minutes following completion of dialysis is 17%. However, some patients exhibit a rebound as high as 45%. This results in a 75% error between KT/V based on immediate post-dialysis BUN measurement and 30 minutes post-dialysis determination. Despite these limitations of the single-pool KT/V model based on the immediate post-dialysis BUN, the need to obtain the post-dialysis BUN sample 30 to 60 minutes after the completion of dialysis in order to compute the more accurate double-pool KT/V, is impractical in the out-patient hemodialysis setting.

At least two methods for approximating the equilibrated or double-pool KT/Vd have been proposed in the literature. The Smye formula approximates the equilibration BUN concentration based on three urea measurements, the usual pre- and post-dialysis determinations, as well as a mid-dialysis blood sample. This method yields an average error of 13% between the estimated equilibration KT/V and the true equilibrated value. The Daugirdas formulas are based on linear transformations of the single-pool KT/V modified according to the type of vascular access; venous shunt or arterial shunt. The improvement of accuracy is comparable to the Smye method.

Despite limitations of the single pool technique, the NKF recommends its use because of the impracticality of the late measurement of urea in the out-patient setting and the unproven accuracy of the double pool estimates.

Living human tissue and blood is recognized as a dynamic system containing a multitude of components and analyte information that is particularly useful in the medical profession for diagnosing, treating and monitoring human physical conditions. To this end, effort has been directed toward developing methods for non-invasive measurement of tissue and blood constituents using spectroscopy. The spectrographic analysis of living tissue has been focused on the identification of spectral information that defines individual analytes and relating such spectral data to the analyte's concentration. Concentration of these analytes vary with time in an individual patient. Acquiring tissue spectral data with sufficient accuracy for use in diagnosis and treatment has proven difficult. Difficulties in conducting the analysis have been found, which are related to the fact that the tissue system is a complex matrix of materials with differing refractive indices and absorption properties. Further, because the constituents of interest are many times present at very low concentrations, high concentration constituents, such as water, have had a detrimental impact on identifying the low level constituent spectral information and giving an accurate reading of the desired constituent concentration.

Improved methods and apparatus for gathering and analyzing a near-infrared tissue spectra for an analyte concentration are disclosed in commonly assigned U.S. Patent applications and issued patents. U.S. Pat. No. 5,655,530 and U.S. patent application Ser. No. 08/844,501, filed Apr. 18, 1997, entitled "Method for Non-invasive Blood Analyte Measurement with Improved Optical Interface" relate to near-infrared analysis of a tissue analyte concentration which varies with time, with a primary focus on glucose concentrations in diabetic individuals. The methods and apparatus include placing a refractive index-matching medium between a sensor and the skin to improve the accuracy and repeatability of testing. U.S. patent application Ser. No. 09/174,812, filed Oct. 19, 1998, entitled "Method for Non-Invasive Blood Analyte Measurement with Improved Optical Interface" discloses additional improvements in non-invasive living tissue analyte analysis. The disclosure of each of these three applications or patents are hereby incorporated by reference.

U.S. Pat. No. 5,636,633 relates, in part, to another aspect of accurate non-invasive measurement of an analyte concentration. The apparatus includes a device having transparent and reflective quadrants for separating diffuse reflected light from specular reflected light. Incident light projected into the skin results in specular and diffuse reflected light coming back from the skin. Specular reflected light has little or no useful information and is preferably removed prior to collection. U.S. patent application Ser. No. 08/871,366, filed Jun. 9, 1997 now Pat. No. 5,935,062, entitled "Improved Diffuse Reflectance Monitoring Apparatus", discloses a further improvement for accurate analyte concentration analysis which includes a blocking blade device for separating diffuse reflected light from specular reflected light. The blade allows light from the deeper, inner dermis layer to be captured, rejecting light from the surface, epidermis layer, where the epidermis layer has much less analyte information than the inner dermis layer, and contributes noise. The blade traps specular reflections as well as diffuse reflections from the epidermis. The disclosures of the above patent and application, which are assigned to the assignee of the present application, are also incorporated herein by reference.

SUMMARY OF THE INVENTION

The present invention is directed to a method and apparatus to directly measure the urea concentration of patients undergoing dialysis, using reflectance, non-invasive near-infrared (NIR) spectroscopy. Thus, instead of drawing blood samples from the patient at the beginning and end of dialysis for analysis of BUN concentrations at a clinical laboratory, the patient's skin will be "scanned" and BUN concentration determined in real-time. This will allow the calculation of dialysis dose or KT/Vd to be measured and reported by the end of the dialysis session.

In its broadest sense, the present invention includes a method for assessing the need for hemodialysis, the progress of a hemodialysis procedure or the adequacy of a hemodialysis treatment. The method generally includes providing a means for optical analysis of tissue on a patient with the means for optical analysis providing an output spectrum at multiple wavelengths. Tissue, as defined herein, includes all tissue components found in a given cross section that is optically penetrated during analysis. The tissue is chiefly made up of extravascular water, which includes both interstitial and intracellular fluid, with a relatively small fraction comprising blood. The output spectrum has varying intensities as related to absorption by the non-vascular tissue. The tissue is coupled to the means for optical analysis, and an output spectrum is acquired before, during or after hemodialysis. The tissue urea concentration, in contrast to blood urea concentration, is calculated from a mathematical model relating the output spectrum to the tissue urea concentration.

In the most limited case, the method and apparatus of the present invention would be used in dialysis centers to measure the pre- and post-dialysis urea levels of patients for real-time KT/V calculations. In a preferred method, measurement can also be made continuously for more detailed urea removal modeling or for feedback to the dialysis unit for feedback and control purposes.

The advantages of the method of the present invention over the standard method of calculation of KT/V by pre- and post-dialysis blood sample BUN measurement are four-fold. First, the accuracy of the calculation of KT/V measured at the end of dialysis approaches the accuracy of KT/V based on post equilibrium blood sample BUN measurements. This is due to the fact that the analysis is of tissue versus blood. The tissue has a relatively small (and negative) urea rebound. Because the tissue water is both chiefly extravascular and much of it is relatively poorly vascularized, its urea content more closely correlates with equilibrated total body urea and equilibrated blood sample BUN than does the immediate post-dialysis, pre-rebound blood sample BUN. Thus, the non-invasive skin measurement of urea delivers the accuracy of the equilibrated or two-pool KT/V, but does not require that the dialysis patient and staff wait 30 minutes or more after dialysis before collecting a final blood sample.

Second, calculation of KT/V is nearly "real-time". The clinician or staff overseeing the dialysis session will be able to judge the efficacy or adequacy of the dialysis dose at the time it is delivered in a "point of care" mode. Failure to deliver the prescribed dose can be appreciated before the patient leaves the dialysis clinic. A decision can then be made to continue the current session or adjust the following dialysis session dose. Should the machine be devoted to a single patient during dialysis, true, real-time kinetic modeling is possible.

Third, the non-invasive nature of the measurement limits the exposure of nursing and technical staff to blood born infectious agents. Two blood samples must be removed from the closed loop hemodialysis circuit and transferred to standard blood analysis tubes in order to calculate the KT/V. In an average hemodialysis centers, where 100 clients are dialyzed, at least 200 blood samples are drawn and sent via courier to a clinical chemistry laboratory. Replacement of blood sample BUN measurements by non-invasive skin measurements would substantially reduce the potential of infection of both the nursing staff who draw blood samples and laboratory personnel who then handle the specimens.

Finally, a fourth advantage over the current methods is a reduction of the cost per measurement. Although the investment in such a device will have to be considered in terms of the fixed reimbursement for monthly measures of KT/V, the clinician will not incur significant costs by using the device more often than once per month. In fact, like the usual blood pressure measurement at the end of a dialysis session, a non-invasive measure of urea would require no reoccurring costs except the time to make the measurement. Dialysis patients would greatly benefit from more frequent measurement of the dialysis dose.

Success of the method of the present invention is believed tied to two components. First, the method incorporates an apparatus and technique for accurately and repeatably acquiring a tissue spectra which is both stable and sensitive to slight changes in spectral output at desired wavelengths and optimizes optical throughput both into and out of the tissue sample. Second, because the spectral features, which can be correlated to tissue urea concentration are not readily apparent from the spectral data, a mathematical model is utilized to correlate spectral data to a tissue urea concentration. The model is built based on multiple tissue scans and same time blood sample BUN measurements. The method preferably incorporates a resultant mathematical model based on Partial Least Squares Algorithm applied to the multiple tissue scans and concomitant BUN measurements which is then applied to an unknown spectra.

The present invention, thus, includes a method for measuring tissue urea concentration of an individual before, during or just after hemodialysis using non-invasive tissue spectroscopy. A preferred method and apparatus illuminates skin with near infrared radiation and collects the reflected, non-absorbed near infrared radiation. Diffuse, rather than specular, reflected light is preferably collected, more preferably light diffusely reflected from the inner dermis rather than the epidermis. For illustrative purposes, three methods are set forth for capturing light diffusely reflected from the inner dermis, including a blocker blade, use of blocking and free zones in a lens or mirror surface, and use of an index matching medium to coat tissue. The near infrared spectra collected can be stored in a computer database.

The method for non-invasively measuring the concentration of urea in tissue includes first providing an apparatus for measuring infrared absorption by a urea containing tissue. The apparatus includes generally three elements, an energy source, a sensor element, and a spectrum analyzer. The sensor element includes an input element and an output element. The input element is operatively connected to the energy source by a first means for transmitting infrared energy. The output element is operatively connected to the spectrum analyzer by a second means for transmitting infrared energy.

In preferred embodiments, the input element and output element comprise lens systems which focus the infrared light energy to and from the sample. In a preferred embodiment, the input element and output element comprise a single lens system which is utilized for both input of infrared light energy from the energy source and output of both specular and diffusely reflected light energy from the analyte-containing sample. Alternatively, the input element and output element can comprise two lens systems, placed on opposing sides of an analyte-containing sample, wherein light energy from the energy source is transmitted to the input element and light energy transmitted through the urea-containing sample then passes through the output element to the spectrum analyzer.

The first means for transmitting infrared energy, in preferred embodiments, simply includes placing the infrared energy source proximate to the input element so that light energy from the source is transmitted via the air to the input element. Further, in preferred embodiments, the second means for transmitting infrared energy preferably includes a single mirror or system of mirrors which direct the light energy exiting the output element through the air to the spectrum analyzer.

In practicing the method of the present invention, a urea-containing tissue area is selected as the point of analysis. This area can include the skin surface on the finger, earlobe, forearm or any other skin surface. Preferably, the urea-containing tissue is the underside of the forearm.

A quantity of an index-matching medium or fluid is then placed on the skin area to be analyzed. The index-matching fluid detailed herein is selected to optimize introduction of light into the tissue, reduce specular light and effectively get light out of the tissue. The medium or fluid preferably contains an additive which confirm proper coupling to the skin surface by a proper fluid, thus assuring the integrity of test data. It is preferred that the index-matching medium is non-toxic and has a spectral signature in the near-infrared region which is minimal, and is thus minimally absorbing of light energy having wavelengths relevant to the urea being measured. In preferred embodiments, the index-matching medium has a refractive index of about 1.38. Further, the refractive index of the medium is preferably constant throughout the composition.

The sensor element, which includes the input element and the output element, is then placed in contact with the index-matching medium. In this way, the input element and output element are coupled to the urea-containing tissue or skin surface via the index-matching medium which eliminates the need for the light energy to propagate through air or pockets of air due to irregularities in the skin surface.

In analyzing for the concentration of urea in the tissue, light energy from the energy source is transmitted via the first means for transmitting infrared energy into the input element. The light energy is transmitted from the input element through the index-matching medium to the skin surface. Some of the light energy contacting the analyte-containing sample is differentially absorbed by the various components and analytes contained therein at various depths within the sample. Some of the light energy is also transmitted through the sample. However, a quantity of light energy is reflected back to the output element. In a preferred embodiment, the non-absorbed or non-transmitted light energy is reflected back to the output element upon propagating through the index-matching medium. This reflected light energy includes both diffusely reflected light energy and specularly reflected light energy. Specularly reflected light energy is that which reflects from the surface of the sample and contains little or no analyte information, while diffusely reflected light energy is that which reflects from deeper within the sample, wherein the analytes are present.

In preferred embodiments, the specularly reflected light energy is separated from the diffusely reflected light energy. The non-absorbed diffusely reflected light energy is then transmitted via the second means for transmitting infrared energy to the spectrum analyzer. As detailed below, the spectrum analyzer preferably utilizes a computer to generate a urea concentration utilizing the measured intensities, a calibration model, and a multivariate algorithm.

The computer includes a memory having stored therein a multivariate calibration model empirically relating the known urea concentration in a set of calibration samples to the measure intensity variations from the calibration samples, at several wavelengths. Such a model is constructed using techniques known by statisticians.

The computer predicts the analyte concentration of the urea-containing sample by utilizing the measure intensity variations, calibration model and a multivariate algorithm. Preferably, the computation is made by the partial least square technique as disclosed by Robinson et al. in U.S. Pat. No. 4,975,581, incorporated herein by reference.

These and various other advantages and features of novelty which characterize the present invention are pointed out with particularity in the claims annexed hereto and forming a part hereof. However, for a better understanding of the invention, its advantages, and the object obtained by its use, reference should be made to the drawings which form a further part hereof, and to the accompanying descriptive matter in which there are illustrated and described preferred embodiments of the present invention.

BRIEF DESCRIPTION OF THE DRAWINGS

In the drawings, in which like reference numerals indicate corresponding parts or elements of preferred embodiments of the present invention throughout the several views.

DETAILED DESCRIPTION OF THE PREFERRED EMBODIMENTS

Detailed embodiments of the present invention are disclosed herein. However, it is to be understood that the disclosed embodiments are merely exemplary of the present invention which may be embodied in various systems. Therefore, specific details disclosed herein are not to be interpreted as limiting, but rather as a basis for the claims and as a representative basis for teaching one of skill in the art to variously practice the invention.

The present invention is directed to an apparatus and method for directly measuring the urea concentration in tissue of patients undergoing or just completing dialysis. The method utilizes reflectance, non-invasive near-infrared spectroscopy. Thus, instead of drawing blood samples from a patient at the beginning and end of dialysis for analysis of blood sample urea concentrations at a clinical laboratory, the patient's skin is scanned and urea concentrations determined in real time.

The present invention is directed toward a method and apparatus which overcomes the deficiencies in present dialysis related to blood urea rebound subsequent to termination of a dialysis procedure. The rebound is caused by the fact that a blood sample is drawn at a time when the blood urea has not equilibrated with the interstitial and intracellular urea. This phenomena is depicted graphically in FIG. 1 and reference should be made thereto. Release of sequestered urea from the intracellular space to the extracellular space continues for about 30 to about 60 minutes after completion of a dialysis session. This equilibration is due to the removal of urea from the blood by the dialyzer at a rate that exceeds the rate at which the urea diffuses from the intracellular to the extracellular compartment. These delays are further associated with the fact that 70% of the total body water is contained in organs that receive only 20% of the cardiac output. Thus, the urea may be trapped in relatively poorly perfused tissues, such as skin, muscle and bone, and are cleared of urea much less efficiently than the highly vascularized organs, such as the liver or lungs.

Figure 1:
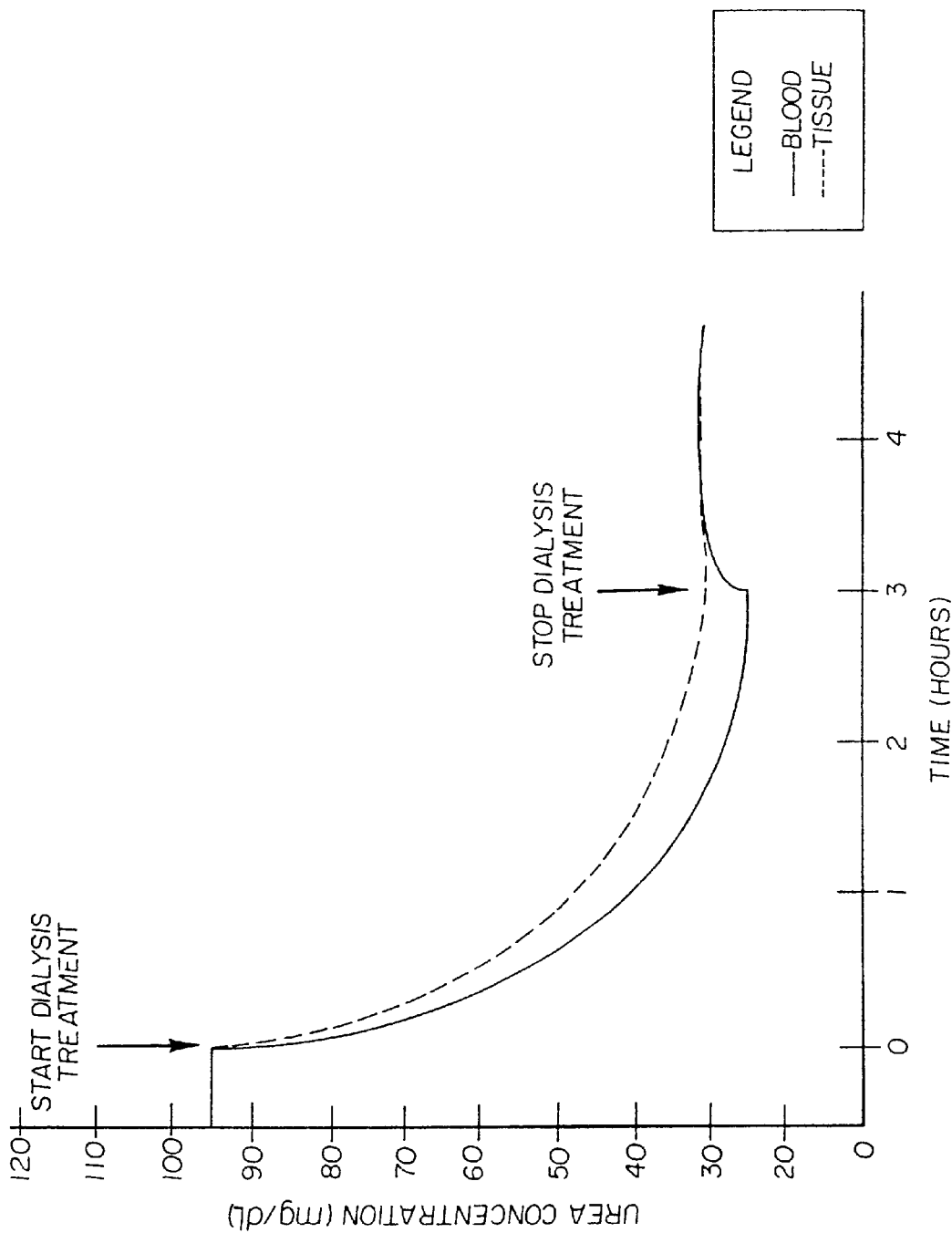
FIG. 1 is a graphical representation of blood urea versus tissue urea concentrations during dialysis and illustrating the rebound effect.

As indicated in FIG. 1, the blood urea concentration follows a curve of reduction during dialysis which shows a relatively sharp upward bump at the time dialysis is terminated. In contrast, tissue urea analysis is indicated as a relatively constant curve and believed to have a small negative bump in urea concentration at the time dialysis is terminated due to continued movement of urea from the intracellular to the extracellular compartment and subsequently to the vascular space. This bump is, however, highly attenuated due to the vast difference in volume of the blood versus the extracellular and intracellular compartments.

If the urea rebound was constant and predictable, it would be relatively easy to compensate for such rebound through blood analysis of urea concentration. However, the magnitude of urea rebound varies greatly among dialysis patients and also varies for the same patient between dialysis sessions. Further, the amount of rebound may also be affected by the efficiency of the dialysis unit during any given procedure. It has been shown that the average rebound at 30 minutes after completion of dialysis is 17%. However, some patients exhibit a rebound as a high as 45%, which results in a 75% error in calculating the urea concentration 30 minutes post-dialysis.

The present invention is based on Applicant's recognition that an accurate, precise and repeatable tissue spectra in the near-infrared range contains spectral features which may be used to model and calculate tissue urea concentration for an individual. The present invention is further based on a recognition that proper analysis, utilizing a model built on multiple scans, can identify these features which are not readily apparent in visual analysis of a spectral output.

As previously stated, there are two components to the success of the method of the present invention. First, the method incorporates an apparatus and technique to accurately and repeatably acquire a tissue spectra. The apparatus is sensitive to slight changes in spectral output at any given wavelength of input and optimizes the overall optical throughput both into and out of the tissue sample. Second, the method requires an analysis tool including a calibration model based on multiple spectral results of known urea concentration which is used to calculate urea concentration in an unknown sample. Each component of the apparatus and method of the present invention are detailed below.

The present invention utilizes an accurate, repeatable and sensitive method for non-invasive measurement of a near-infrared tissue spectra. It is recognized that the sample is a complex matrix of materials with differing refractive indices and absorption properties. Further, because many constituents are present at very low concentrations, it has been found to be imperative to couple light into and out from the tissue in an efficient manner. The method of the present invention incorporates an index-matching medium, fluid or deformable solid, to improve the efficiency of coupling the light both into and out of the tissue sample.

The present invention utilizes light energy in the near-infrared region of the optical spectrum as an energy source for analysis. Water is by far the largest contributor to absorption in tissue in the near-infrared region because of its concentration, as well as its strong absorption coefficient. It has been found that the total absorption spectrum of tissue, therefore, closely resembles the water spectrum. It has been further found that tissue greatly scatters light because there are many refractive index discontinuities in a typical tissue sample. Water is perfused through the tissue, with a refractive index of 1.33. Cell walls and other features of tissue have refractive indices closer to 1.5 to 1.6. These refractive index discontinuities give rise to scatter. Although these refractive index discontinuities are frequent, they are also typically small in magnitude and the scatter generally has a strong directionality towards the forward direction.

This forward scatter has been described in terms of anisotropy, which is defined as the cosine of the average scatter angle. Thus, for complete backwards scatter, meaning that all scatter events would cause a photon to divert its direction of travel by 180 degrees, the anisotropy factor is −1. Likewise, for complete forward scatter, the anisotropy factor is +1. In the near-infrared, tissue has been found to have an anisotropy factor of around 0.9 to 0.95, which is very forward scattering. For instance, an anisotropy factor of 0.9 means that an average photon of light only scatters through an angle of up to 25 degrees as it passes through the sample.

In acquiring a tissue spectra, measurements can be made in at least two different modes. It is recognized that one can measure light transmitted through a section of tissue, or one may measure light reflected or remitted from tissue. It has been recognized that transmission is the preferred method of analysis in spectroscopy because of the forward scattering of light as it passes through the tissue. However, it is difficult to find a part of the body which is optically thin enough to pass near-infrared light through, especially at the longer wave lengths. Thus, the preferred method for measurement in the present invention is to focus on the reflectance of light from the sample.

Photons reflect and refract at refractive index discontinuities, and so light impinging on tissue immediately has a small reflectance at the tissue surface. This is referred to as specular reflectance. Since this light does not penetrate into the tissue, it contains little information about the tissue constituents. This is especially true in light of the physiology of skin, which possess an outward layer which is essentially dead and lacks current information about the patient's physiological state. Thus, reflected light energy containing spectral data for urea analysis is believed to be that light which is reflected back to the surface through refractive index discontinuities deeper within the tissue sample. This reflected light energy is referred to as diffusely reflected light.

Applicants have found that a large fraction of incident photons are absorbed in the tissue. Those photons which are available for coupling back out of the tissue are likely diverted in their angular path. In fact, by definition, a photon must change direction in order to exit the tissue in a direction towards the input optic. Applicants, however, have found that a large problem with detection is associated with the refractive index discontinuity between the average tissue refractive index and the refractive index of air outside of the tissue. It has been found that this discontinuity acting on incident light leads to a refraction and a small specular reflectance of less than about 5 percent. However, on the way out, the discontinuity gives rise to a critical angle phenomenon. Because the photon is traveling from a high refractive index medium to a lower one, a critical angle exists above which a photon is totally internally reflected and will not escape the tissue sample. This critical angle for photons traveling from tissue to air has been found to be about 46 degrees, which presents a problem. A photon normally incident on the tissue surface must deviate through a large angle to exit. Because of the forward directionality of scattering, this is difficult for a photon to do, and it is very likely to make a grazing or high angle incidence with the tissue and air interface. The grazing incidence photons will not escape because the critical angle is exceeded.

Applicants have found a solution for the differences in refractive index associated with coupling light energy exiting tissue to an analytical instrument. The solution is the use of an immersion fluid which has very low absorptivity in the spectral range of interest, and has a viscosity compatible with good flow and coverage, while having a refractive index which closely matches tissue. In preferred embodiments, the index-matching fluid is preferably minimally or essentially non-absorbing of light energy in the wavelengths selected as relevant to measurement of urea concentration. The fluid is thus non-spectroscopically active at desired wavelengths. However, it is believed a minimally absorbing index-matching fluid, for example one that absorbs less than about 10% of the light energy of relevant wavelengths, could still be utilized. A preferred material is a fluorinated, chlorinated hydrocarbon polymer oil manufactured by Occidental Chemical under the tradename FLUOROLUBE. FS5 is a preferred FLUOROLUBE. These oils have a refractive index of about 1.38, are non-toxic, and Applicants have found that it has a spectral signature in the near-infrared region which is minimal.

Figure 2:
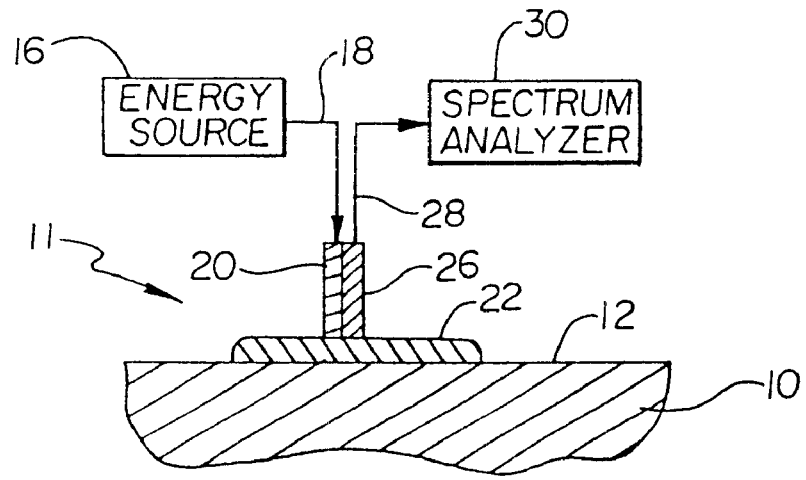
FIG. 2 is a partial cross-sectional view of a sensor element coupled to the skin surface via an indexing-matching fluid.
Figure 3:
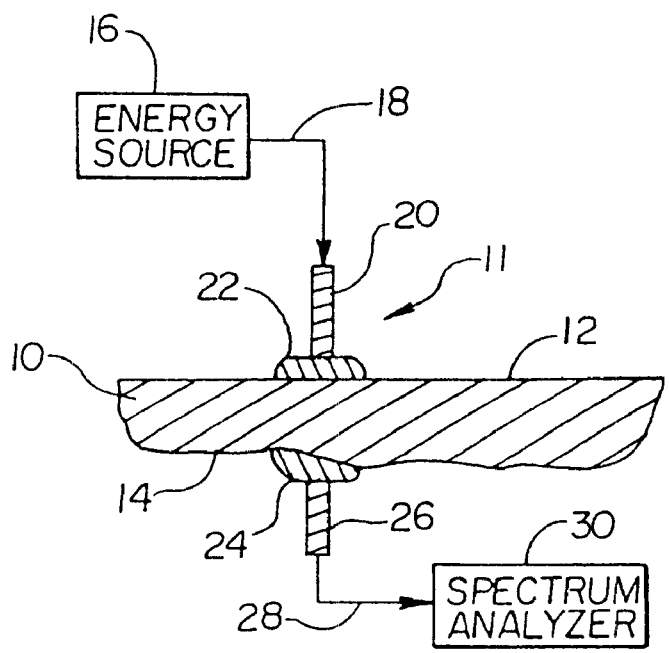
FIG. 3 is a partial cross-sectional view of an alternative embodiment of a sensor element coupled to opposite sides of a skin surface via an indexing-matching fluid.

Now referring to FIGS. 2 and 3, partial cross-sectional views of two preferred embodiments of an apparatus for non-invasively acquiring a tissue spectrum are depicted. The depictions in FIGS. 2 and 3 are schematic to depict the concept of utilizing an index-matching medium 22 in conjunction with a non-invasive sensor element 11 operatively connected to an energy source 16 and a spectrum analyzer 30. The relative size, shape and detail of physical components are not depicted.

The apparatus depicted in FIG. 2 and the apparatus depicted in FIG. 3 generally include three elements, an energy source 16, a sensor element 11, and a spectrum analyzer 30. The embodiment of FIG. 2 depicts the sensor element as including an input element 20 and an output element 26, which can include a single lens system for both input and output light energy. The input element 20 and output element 26 are in contact with a common skin surface 12 of the selected tissue 10. The alternative embodiment of FIG. 3 depicts an alternative sensor element 11 arrangement, wherein the input element 20 and output element 26 are arranged on opposing surfaces 12, 14 of tissue 10. Both embodiments function to give a measure of the absorption of infrared energy by the tissue 10. However, the embodiment of FIG. 2 is utilized to measure the quantity of light energy which is reflected from the tissue 10 by the components or features therein. In contrast, the embodiment of FIG. 3 measures the transmission of light energy through the tissue 10. In either embodiment, the absorption at various wavelengths can be determined by comparison to the intensity of the light energy from the energy source 16.

The energy source 16 is preferably a wide band, infrared black body source. The optical wavelengths emitted from the energy source 16 are preferably between 1.0 and 2.5 µm. The energy source 16 is operatively coupled to a first means for transmitting infrared energy 18 from the energy source to the input element 20. In preferred embodiments, this first means 18 is simply the transmission of light energy to the input element 20 through air by placing the energy source 16 proximate the input element 20.

The input element 20 of the sensor element 11 is preferably an optical lens which focuses the light energy to a high energy density spot. However, it is understood that other beam focusing means may be utilized in conjunction with the optical lens to alter the area of illumination. For example, a multiple lens system, tapered fibers, or other conventional optical beam-shaping devices could be utilized to alter the input light energy.

In both embodiments depicted in FIGS. 2 and 3, an output sensor 26 is utilized to receive reflected or transmitted light energy from the tissue 10. As described in conjunction with a method of analysis below, the embodiment of FIG. 2 has an output sensor 26 which receives reflected light energy, while the embodiment of FIG. 3 includes an output sensor 26 which receives transmitted light through the tissue 10. As with the input element 20, the output element 26 is preferably an optical lens. Other optical collection means may be incorporated into an output element 26, such as a multiple lens system, tapered fiber, or other beam-collection means to assist in directing the light energy to the spectrum analyzer 30.

A second means for transmitting infrared energy 28 is operatively connected to the output element 26. The light transmitted through the second means for transmitting infrared energy 28 is transmitted to the spectrum analyzer 30. In a preferred embodiment, the operative connection to the output element includes transmission of the reflected or transmitted light energy exiting the output element through air to the spectrum analyzer 30. A mirror or series of mirrors may be utilized to direct this light energy to the spectrum analyzer. In a preferred embodiment, a specular control device is incorporated to separate the specular reflected light from diffusely reflected light. Such devices are disclosed in co-pending and commonly assigned application Ser. No. 08/871,366, filed Jun. 9, 1997 now Pat. No. 5,935,062, and entitled "Diffuse Reflectance Monitoring Apparatus", the disclosure of which is incorporated herein by reference.

In practicing the method of the present invention, tissue 10 area is selected as the point of analysis. This area can include the skin surface 12 on the finger, earlobe, forearm, or any other skin surface. Preferably, the area for sampling includes blood vessels near the surface, and a relatively smooth, uncalloused surface. A preferred sample location is the underside of the forearm. A quantity of an index-matching medium 22, whether fluid or deformable solid, is then placed on the skin surface 12 in the area to be analyzed to couple the sensor element 11, which includes the input element 20 and the output element 26 to the instrument.

In acquiring a spectra of the tissue 10, light energy from the energy source 16 is transmitted through the first means for transmitting infrared energy 18 into the input element 20. The light energy is transmitted from the input element 20 through the index-matching medium 22, to the skin surface 12. The light energy contacting the skin surface 12 is differentially absorbed by the various components and analytes, such as the urea of interest, contained below the skin surface 12. In a preferred embodiment, the non-absorbed light energy is reflected back to the output element 26 upon propagating again through the index-matching medium 22. The non-absorbed light energy is transmitted via the second means for transmitting infrared energy 28 to the spectrum analyzer 30.

In the alternative embodiment of FIG. 3, the light energy propagated through the input element 20 and first quantity of index-matching medium 22 is differentially absorbed by the tissue 10, while a quantity of the light energy at various wavelengths is transmitted through the tissue 10 to the opposing or second skin surface 14. From the second skin surface 14, the non-absorbed light energy is propagated through the second quantity of index-matching medium 24 to the output element 26 with subsequent propagation to the spectrum analyzer 30 for producing the tissue spectra.

As previously stated, the index-matching medium 22 of the present invention is a key to the improved accuracy and repeatability of the method described above. The index-matching medium can preferably be a fluid composition containing chlorofluorocarbons. The composition can also be a mixture of chlorofluorocarbons and perfluorocarbons. A preferred composition includes a chlorotrifluoroethylene polymer. A preferred composition contains about 80% to about 99.8% by weight of chlorofluorocarbons. As previously stated, the present invention utilizes an index-matching fluid to optimize the input and output of light energy to and from a tissue to be analyzed. In its broadest sense, the index-matching fluid of the present invention can be any fluid which creates an improved optical interface over that interface which results from simply placing the probe of the present invention on a skin surface. Absent the index-matching fluid of the present invention, this interface can include gaps which are air filled and cause detrimental refraction of light both going into the tissue and exiting the tissue. Thus, any index-matching fluid having a refractive index closer to that of the tissue at about 1.38 versus the refractive index of air of about 1.0 would provide an improved interface.

Applicants have also recognized that the usefulness of the apparatus of the present invention requires that the coupling of the sensor be repeatable and that the results be an accurate reflection of the tissue constituents of the patient. To this end, Applicants have found that it is preferable for the index-matching fluids of the present invention to contain diagnostic additives. The diagnostic additives provide an assessment of the quality of the lens to tissue interface and/or an assessment of the instrument's present performance.

The non-invasive measurement of tissue spectra by the present invention is improved by placing an additive into the index-matching fluid that allows evaluation of the thickness of the fluid when the tissue is placed in contact with the instrument. In preferred embodiments, the additive also provides a calibration of the instrument by including a compound of known high absorption at a specified wavelength of light. Such additives also further assure that the correct index-matching fluid is being utilized for the instrument.

Since an index-matching fluid inherently causes a change of height in the tissue above the sample probe, the measurement of this height can aid in the overall urea analysis, while allowing a path length correction to be applied to the spectral measurement as a function of the tissue height above the sampler. This can insure a reproducible, consistent height is achieved before commencing the spectral measurement of the tissue, and further allows for the adjustment of the height before commencing the spectral measurement of the tissue. In this way, the user can be certain that spurious results are not achieved due to excess matching fluid height, insufficient index-matching fluid being utilized, or some other misplacement of the tissue surface relative to the analyzer.

Laboratory spectrometers utilize a Fourier Transform (FTIR) system which incorporates a laser reference signal to establish the wavelengths and guarantees that the instrument is calibrated. However, it is likely, instruments that are affordable for an end user will not use a laser, but rather will be dispersion type instruments such as gratings, CCD arrays and others. With such instruments, it is important to make certain that calibration is proper prior to each analysis of tissue spectra. To this end, Applicants have found that the addition of an additive which includes a well-defined spectral feature at a known wavelength of light can be utilized to assure calibration.

The use of a known spectrally active additive to the index-matching fluid also insures that the end user is using a correct index-matching fluid for which the instrument has been calibrated and programmed. The use of a different index-matching fluid could result in an error in the non-invasive tissue spectrum by absorbing light energy in the areas of interest for identifying an individual.

To accomplish the above repeatability, accuracy and quality assurance, a spectroscopically active agent is preferably added to the index-matching fluid. The agent preferably has sharp bands of absorption outside the region of interest to be measured. For example, in a preferred method for urea measurement, the agent would be active outside the range of 4200 to 7200 wave numbers. The agent could also be active within this range so long as there is no significant overlap with wavelengths actually used to calculate a tissue urea concentration. The additive can be manufactured by placing an appropriate functional group on perfluorinated hydrocarbons. The perfluorinated hydrocarbons are spectrally inactive in the region of interest, however, the functional group placed upon the perfluorinated hydrocarbons may be spectrally active. Further, these functional groups do not interfere with the analysis of the blood analyte of interest. Exemplary compounds include perfluoro-2-butyltetrahydrofuran and perfluorosuccinyl chloride.

In an alternative embodiment, the index-matching fluid and diagnostic additive can comprise the same fluid which provides both functions. For example, perfluoro-2-butyltetrahydrofuran can be utilized as an index-matching medium which improves the optical interface, and at the same time includes a functional group which makes the compound spectrographically active in a desired range for diagnostic purposes.

Figure 9:
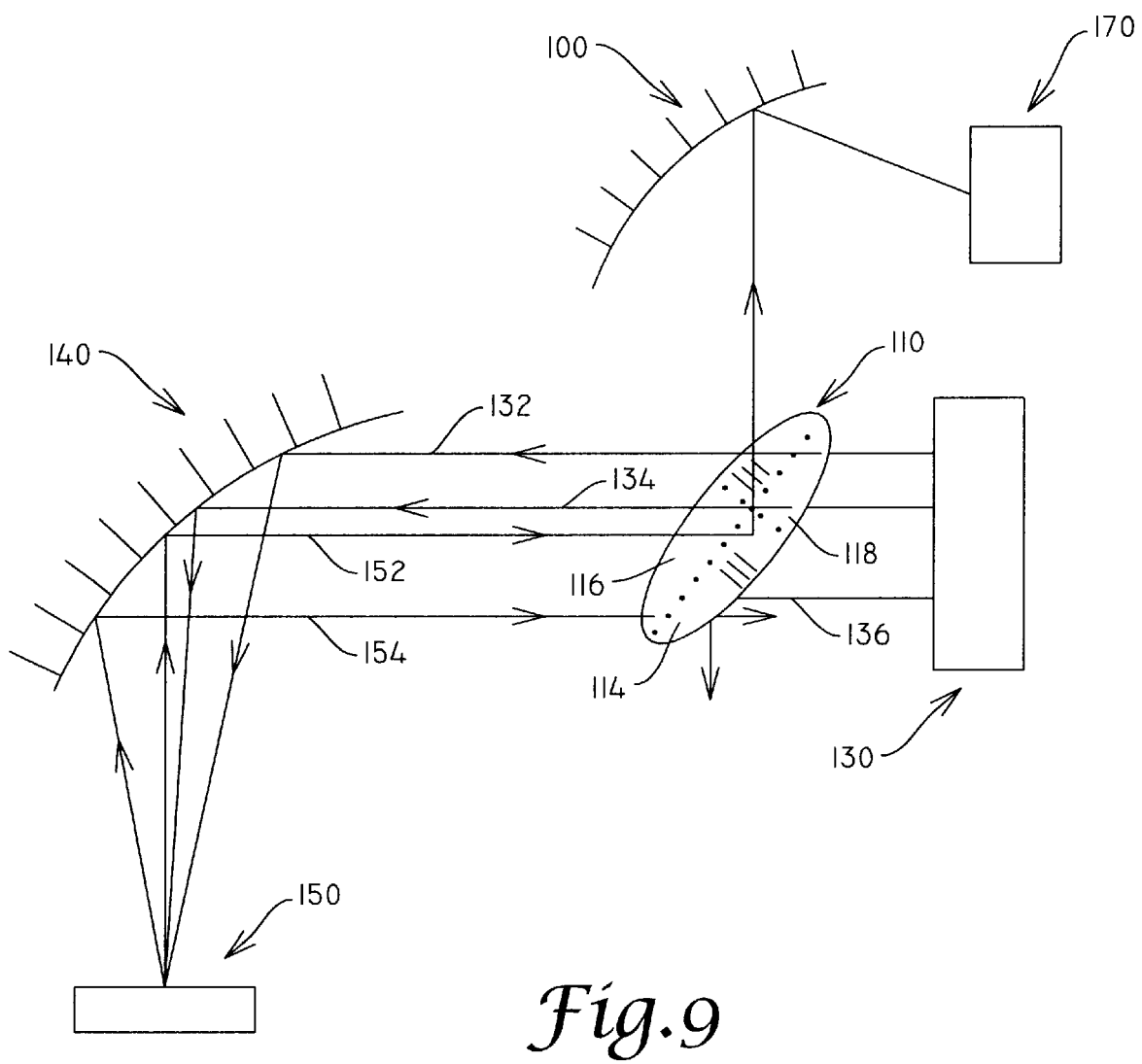
FIG. 9 is a schematic of a diffuse reflectance spectroscopy system.

Referring now to FIG. 9, there is shown a schematic of a diffuse reflectance spectroscopy system designed to facilitate effective light entry into tissue and to reduce the effects of spectral reflectance on gathered spectra. A specular control device 110 is shown having open area 118 and reflective area 114. It is recognized that specular control device 110 may be circular, elliptical, rectangular or any other shape.

A light or energy source 130 is shown for providing an analytical source beam indicated at 132, 134 and 136. Source beam 132, 134 and 136 impinges of a first surface of specular control device 110. That portion of the source beam indicated at 136 is incident to reflecting portion 114 of specular control device 110 and is reflected away as shown by the arrow. That portion of the source beam indicated at 132 and 134 passes through open area 118 of specular control device 110, and continues on to be reflected by an elliptical mirror 140 to a desired focus on sample 150. A diffuse reflectance beam 152 is reflected from sample 150 to mirror 140 and thence to the reflective surface 114 as shown by the arrows. Diffusely reflected beam 152 is reflected onto an elliptical mirror 100 from which it is focused into a detector 170 where the beam is analyzed.

In contrast to the diffusely reflected beam 152, a specularly reflected beam of light 154 is represented in FIG. 9. As is shown in FIG. 9, the specularly reflected beam 154 is reflected from the sample 150 to the mirror 140. This specularly reflected beam then passes through the open area 116 which is the open quadrant opposing the input quadrant 118 through which that light beam entered. The specularly reflected light 154 is thus not reflected into the analyzer 170 as described above for the diffusely reflected beam 152.

Figure 10:
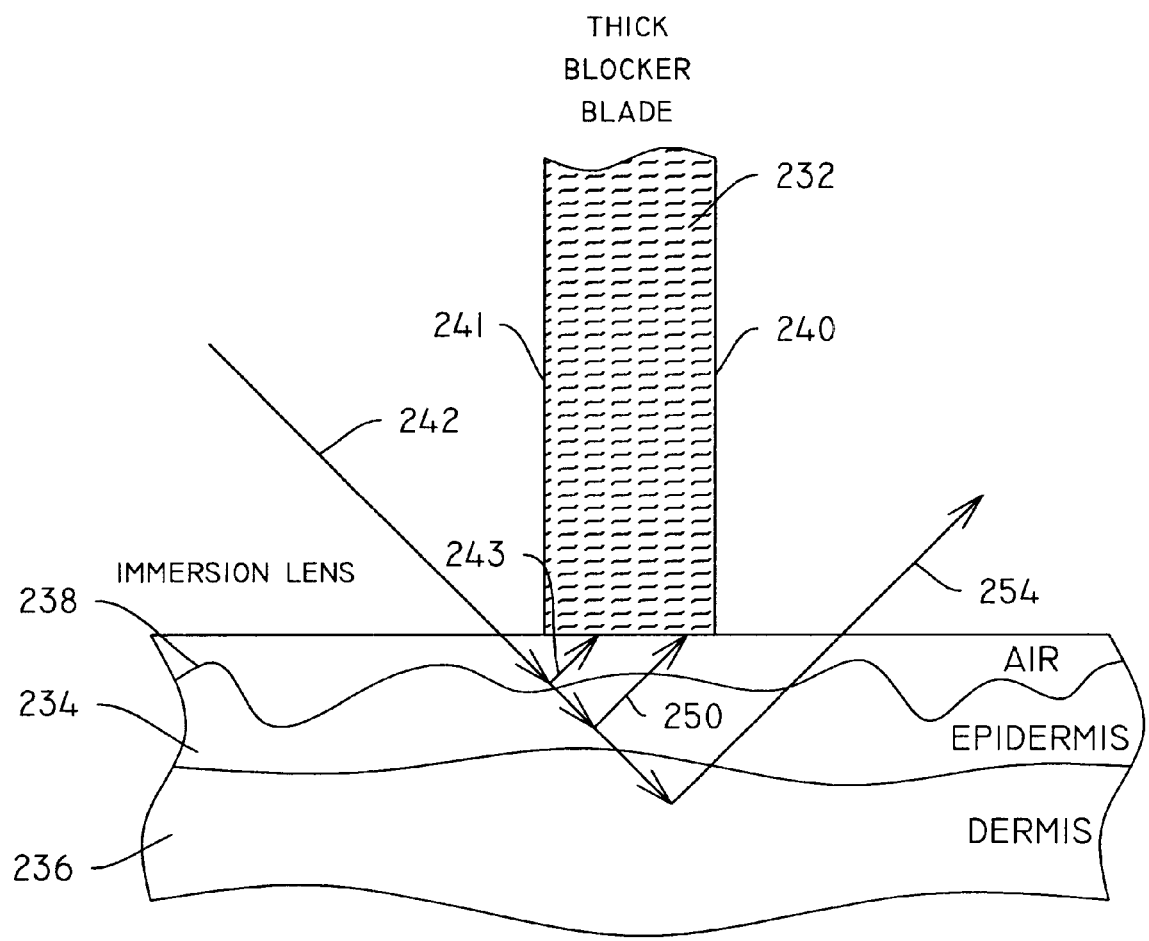
FIG. 10 is a simplified schematic drawing detailing a thick blocker blade.

Referring now to FIG. 10, there is shown a simplified schematic drawing detailing a thick blocker blade. An immersion lens is positioned adjacent to the top surface of a tissue sample. In the illustrative diagram, the tissue sample is human skin having an outer epidermis layer 234 and an inner dermis layer 236. Because the top surface 238 of the tissue sample is rough, gaps will typically be present between at least parts of the immersion lens and the top surface 238 of the tissue sample as shown.

A relatively thick blocker blade 232 is provided. The blocker blade has a back surface 240 and a front surface 241, with a thickness defined therebetween. The tissue sample may include a number of layers, including an epidermis layer 234 and a dermis layer 236. It may be desirable to exclude the diffusely reflected light rays that are reflected by the epidermis layer 243 along with that reflected specularly 250.

To achieve discrimination, the back surface 240 of the blocker blade may be laterally spaced a distance from the illuminated portion of the tissue sample such that the light rays 250 that are diffusely reflected from the epidermis layer 234 are substantially prevented from reaching the spectroscopic analyzer. The epidermis layer 234 may have little or no blood therein, and thus the diffusely reflected light from the epidermis layer 234 tends to contaminate the desired spectrum of the diffusely reflected light 254 from the information rich dermis layer 236. By preventing the diffusely reflected light 250 of the epidermis layer 234 from reaching the spectroscopic analyzer, a contaminated spectrum from the dermis layer 236 can be obtained and analyzed. The front surface 241 of the blocker blade 232 may be positioned directly adjacent the illuminated portion of the tissue sample, within the illuminated portion, or laterally spaced toward the back surface 240 relative to the illuminated portion. The epidermis layer is typically about 40 micrometers to about 400 micrometers in thickness at desired sample areas. It has been found a blocker blade thickness for use in blocking both specular and diffusely reflected light from the epidermis for some application may be 100 micrometers to 800 micrometers, with 400 micrometers considered most useful.

In addition to the above, the thick blocker blade 232 may substantially prevent the specularly reflected component 243 from reaching the spectroscopic analyzer, even when the surface of the sample is not perfectly flat as shown. With a thick blocker blade 232, the leakage of light between the surface of the skin 238 and the blocker blade 232 may be reduced or eliminated. This may imjrpove the quality of the resulting spectrum that is provided to the spectroscopic analyzer.

As can readily be seen, a method for obtaining a diffuse reflectance spectra from human tissue for the non-invasive measurement of blood analytes has been achieved by multiple methods and apparatuses. The method comprising the steps of (a) generating infrared energy; (b) directing the infrared energy to the tissue; and (c) collecting the infrared energy that is reflected from a first depth and rejecting the infrared energy that is reflected from a second depth.

Figure 11:
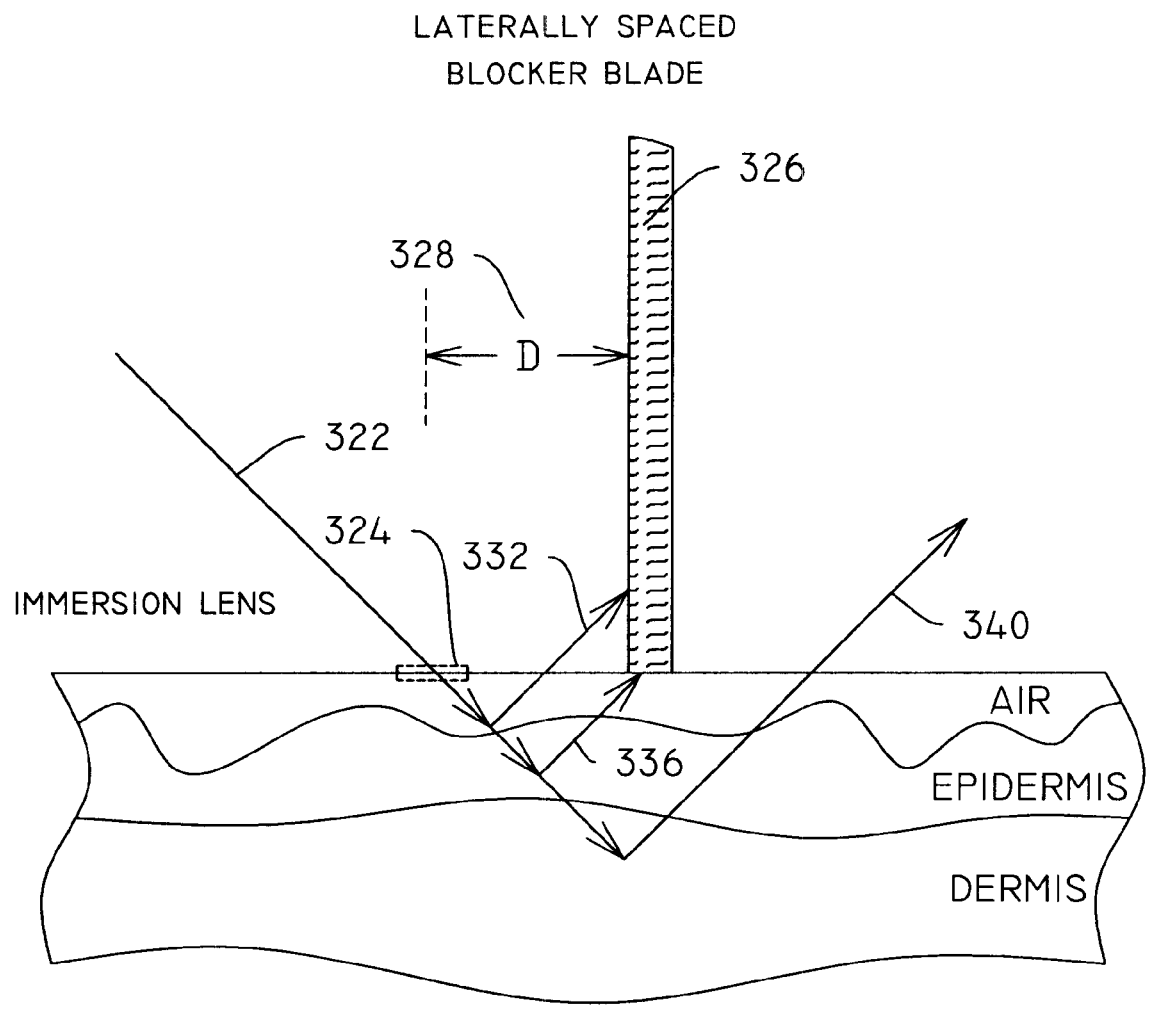
FIG. 11 is a simplified schematic drawing detailing an effectively "thick" blocker blade made from a single thin blocker blade that is laterally spaced from the illuminated spot of the incident light rays.

FIG. 11 is a simplified schematic drawing detailing an effectively "thick" blocker blade made from a single thin blocker blade that is laterally spaced from the illuminated spot of the incident light rays. The immersion lens may focus the incident light 322 onto an illuminated spot 324. In other apparatuses, a second thin blocker blade could be placed adjacent the illuminated spot 324, however, this apparatus does not show such a second blocker blade. The blocker blade 326 may be spaced a sufficient distance "D" 328 from the illuminated spot 324 to prevent both specularly reflected light 332 and any diffusely reflected light 336 provided by the epidermis layer, from reaching the spectroscopic analyzer as diffusely reflected light 340 from the dermis layer does.

The illustrative blocker blade in FIG. 11 shows an apparatus for discriminating between infrared energy that is diffusely reflected from the epidermis layer within the tissue from infrared energy that is diffusely reflected from the dermis layer. The apparatus is sized for substantially preventing infrared energy that is diffusely reflected from the epidermis layer from reaching a collection device.

Figure 4:
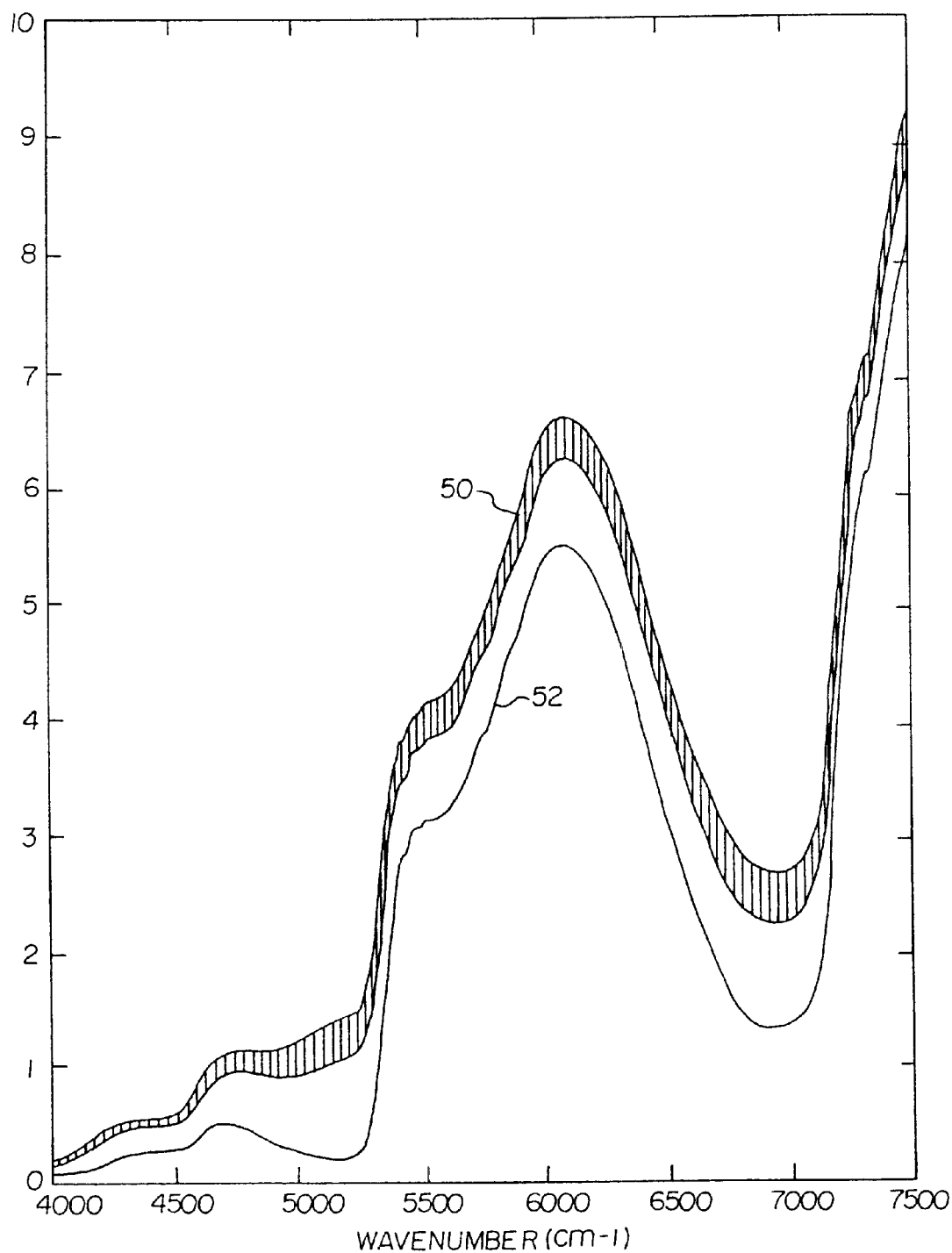
FIG. 4 is a graphical representation of experimental data showing the improvement in accuracy and repeatability of a sensor coupled to the skin via an index-matching medium.

In practicing the present invention, the tissue spectra is determined by measuring the light intensity received by the output sensor at the various wavelengths which give indications of the absorption at such wavelengths of the infrared energy as a function of the composition of the tissue sample. As is well known in the art, a spectrum analyzer 30 of the present invention is able to convert the intensity of the infrared energy incident on the detector into a proportional amplitude of voltage. In this way, an output spectrum is defined for the tissue under analysis. Experimental results documenting the improvements associated with the above-identified method for obtaining a tissue spectra are documented in FIG. 4. The top trace, labeled 50, shows the result obtained when sampling in the previously described mode in the absence of an index-matching medium. In the bottom trace, labeled 52, 100 microliters of chlorotrifuoroethylene polymer was applied to the surface of the input and output device prior to placing the arm. First, each of the lines drawn, 50 and 52, are each comprised of multiple spectra. With the index-matching fluid, all of the spectra overlay each other quite closely. This is a good indication that the interface is quite stable. Without the index-matching medium, the interface is extremely unstable and it is clear that the data at a particular wavelength would not be particularly accurate when dealing with small changes in concentration of specific constituents that would be indicative of an individual's identity.

Once accurate and repeatable spectral data for tissue analysis is acquired, the second key element of the present invention is the methodology for calibrating the device or instrument to identify spectral features or combinations of features that can be utilized to predict tissue urea concentration.

In building the model for urea analysis of the present invention, a computer is utilized which includes a memory having stored therein a multivariate calibration model empirically relating the known urea concentration in a plurality of calibration samples to the measured intensity variations from the calibration samples. The comparisons are conducted at several wavelengths which are defined as having detected intensity variations in response to variations in urea concentration. Such model is constructed using techniques known by statisticians.

The computer predicts the urea concentration of the tissue sample by utilizing the measured intensity variations, the calibration model, and a multi-variant algorithm. Preferably, the computation is made by the partial least squared techniques as disclosed by Robinson et al. in U.S. Pat. No. 4,975,581, incorporated herein by reference.

It has been found that considerable improvement in detection precision is obtained by simultaneously utilizing at least several wavelengths from the entire spectral frequency range of the energy source to derive data for a multi-variant analysis. The multi-variant method allows both detection and compensation for interferences, the detection of meaningless results, as well as for modeling many types of non-linearities. Since the calibration sample used to derive the models have been analyzed on a multi-variant basis, the presence of unknown biological materials in the urea containing tissue does not prevent or distort the analysis. This is because these unknown biological materials are also present in the calibration samples used to form the model. Thus, it is important to the model of the present invention that the samples used to build the model and calibrate the urea analysis are actually samples of living tissue containing other constituents which will be present in varying quantities of any future analysis.

EXPERIMENTAL RESULTS

A series of experiments were conducted to determine the feasibility and capabilities of the present disclosed method and apparatus for optical measurement of the tissue urea concentration. The measurements were all made non-invasively on the skin, sampled in reflectance from the underside of a patient's forearm. The spectrometer utilized was a FTIR spectrometer having a 16 $cm^{-1}$ resolution. The exact spectrometer was a Nicolet Magna near-infrared spectrometer. The methodology utilized is that disclosed previously in the present application. These data were acquired using an FTIR spectrometer in the wavelength region from 4000 $cm^1$ to 8000 $cm^1$. Spectroscopic data was obtained from the underside of the arm and a one minute sample collection period was used.

Figure 5:
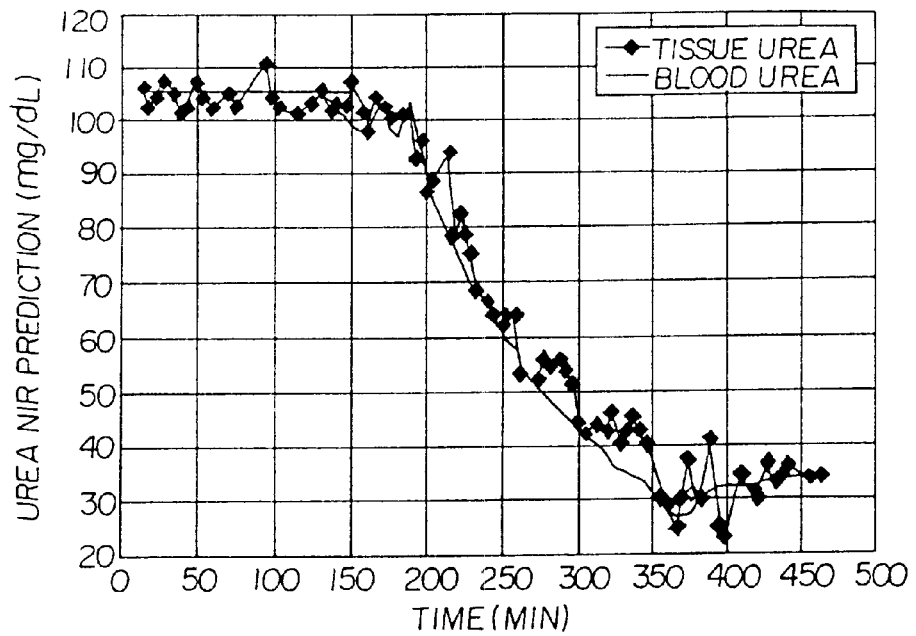
FIG. 5 is a graphical representation of a single patient's experimental data showing blood urea plotted relative to tissue urea predicted by the methods of the present invention.
Figure 7:
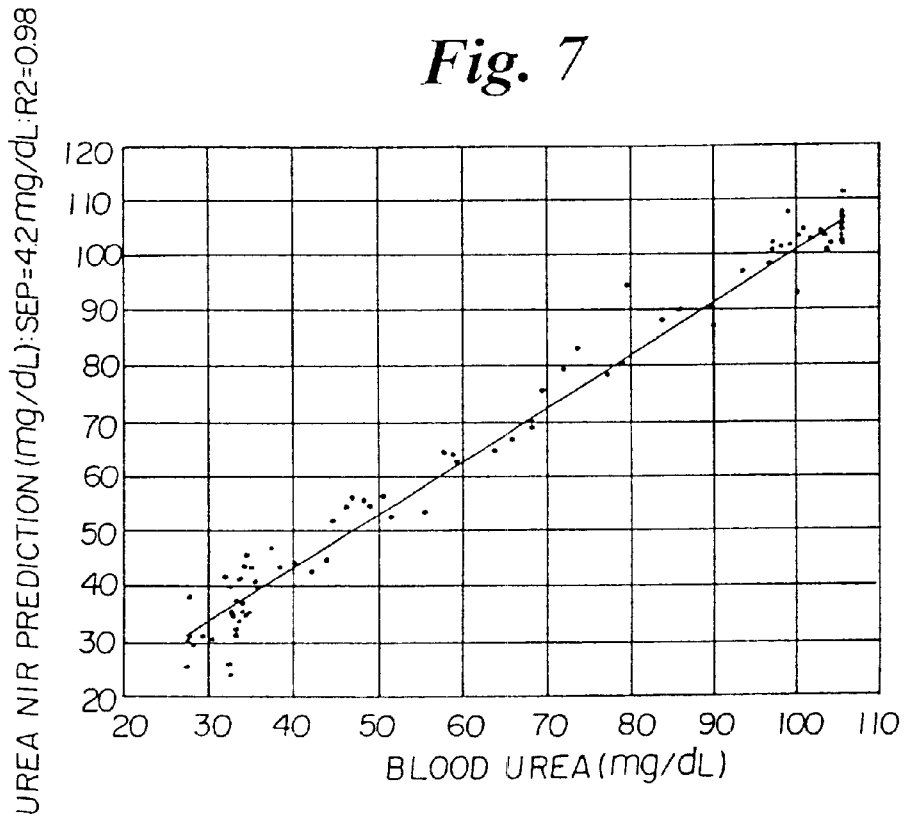
FIG. 7 is a graph showing the blood urea plotted against the tissue urea for the data of FIG. 5.
Figure 6:
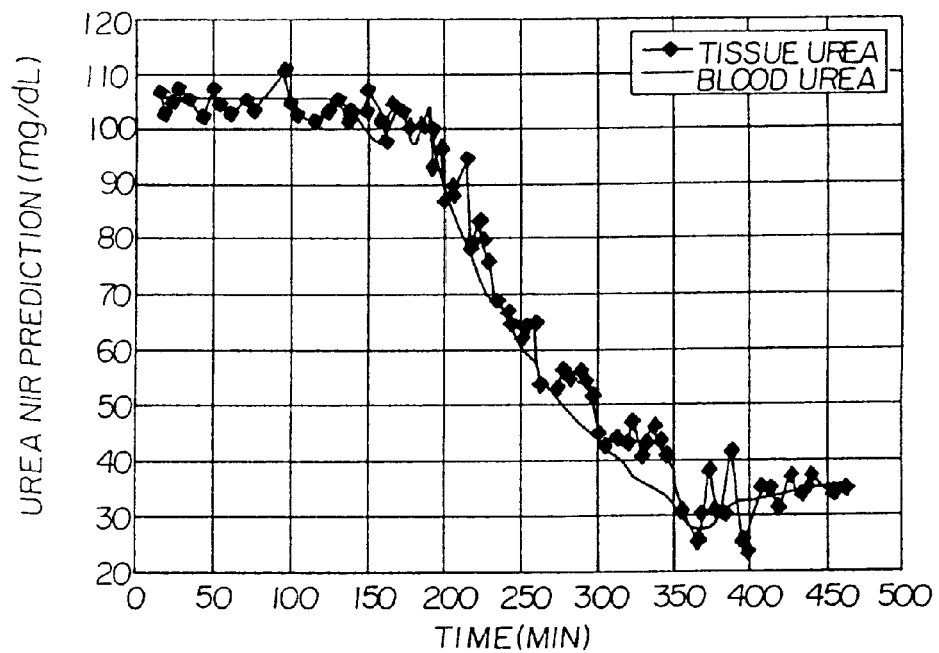
FIG. 6 is a second graphical representation of a second patient's blood urea plotted relative to predicted tissue urea utilizing the methods of the present invention.
Figure 8:
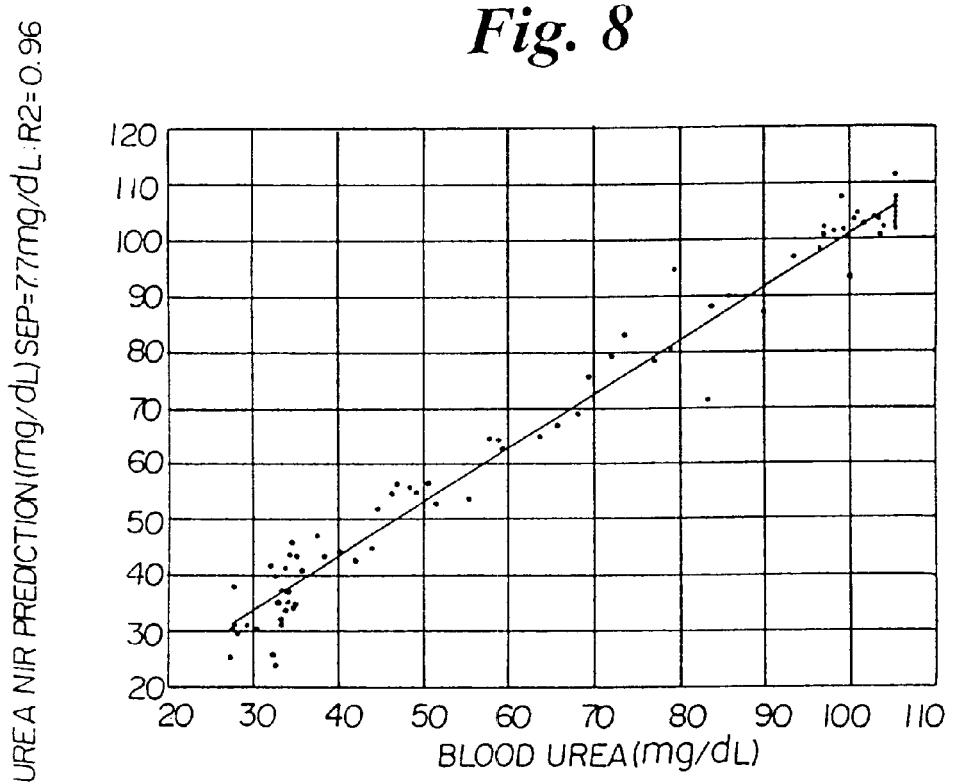
FIG. 8 is a graph showing the blood urea plotted against the tissue urea for the data of FIG. 6.

The experiment included two patients undergoing dialysis therapy. A computer-based calibration model was built for these patients using the partial least squares technique and was subsequently applied during their dialysis treatment. The calibration model was used to generate non-invasive prediction results during dialysis therapy. FIGS. 5 and 6 show the reduction in blood urea concentration as a function of time. Also shown is the reduction in tissue urea concentration as predicted by the calibration model from spectral data acquired during dialysis. FIGS. 7 and 8 show the delay between the blood and the tissue urea levels. As the urea is removed from the blood space, the urea must transfer from the extravascular space to the vascular space. This delay is consistent with what is anticipated due to the fact that the urea is initially removed from the blood and the tissue urea concentration lags behind the blood concentration by a small amount.

In conducting the above set of experiments and in building the calibration model, NIR spectra were collected from a given subject before dialysis, during dialysis and after dialysis. The post-dialysis spectra were taken approximately one hour later to ensure equilibrium between the tissue and blood urea concentrations. The total number of spectra collected before and after the dialysis was about 50 spectra. These data represent tissue spectra of the given subject in which BUN is unchanging. In separate experiments, the absorbance spectrum of pure BUN was obtained from known solutions prepared with varying BUN concentrations. Random amounts of the absorbance spectrum of pure BUN were added mathematically to the BUN-constant spectra from the given subject. This procedure ensured that spectral variation in BUN did not correlate with any other variations present in the BUN-constant subject spectra. The partial least squares multivariate calibration model was then built from these BUN-augmented subject spectra using the spectral region between 4000 and 8000 $cm^{-1}$. The optimal number of PLS factors was determined to be 12 factors. This calibration model was then used to predict the BUN concentration non-invasively from spectra collected from the subject during dialysis. The results of the prediction of BUN from the spectra collected during dialysis are shown in FIGS. 5–8.

New characteristics and advantages of the invention covered by this document have been set forth in the foregoing description. It will be understood, however, that this disclosure is, in many respects, only illustrative. Changes may be made in details, particularly in matters of shape, size, and arrangement of parts, without exceeding the scope of the invention. The scope of the invention is, of course, defined in the language in which the appended claims are expressed.

What is claimed is:

1. A non-invasive method for measuring the concentration of urea in human tissue comprising the steps of:

providing an apparatus for measuring infrared absorption, said apparatus including an energy source emitting infrared energy at multiple wavelengths, including selected wavelengths relevant to urea concentration due to absorption by said urea, and an input element, said apparatus further including an output element; and irradiating said tissue through said input element with said multiple wavelengths of infrared energy before, during or after hemodialysis for assessing the need for hemodialysis, the progress of a hemodialysis procedure or the adequacy of the hemodialysis treatment, respectively, and collecting and subsequently measuring at least a portion of the non-absorbed infrared energy with said output element to predict said tissue urea concentration by use of a multivariate algorithm.

2. The method of claim 1, wherein said selected wavelengths include the range of about 4000 $cm^{-1}$ to about 8000 $cm^{-1}$, and wherein said irradiating step and said collecting step are performed using infrared energy within said range.

3. A non-invasive method for measuring the concentration of urea in analyte-containing human tissue comprising the steps of:

providing an optical apparatus for measuring infrared absorption, said apparatus including an energy source emitting infrared energy at multiple wavelengths, including selected wavelengths relevant to urea concentration due to absorption by said urea, operatively connected to an input element, said apparatus further including an output element operatively connected to a spectrum analyzer;

irradiating said tissue through said input element with multiple wavelengths of infrared energy before, during or after hemodialysis for assessing the need for hemodialysis, the progress of a hemodialysis procedure or the adequacy of the hemodialysis treatment, respectively; and collecting at least a portion of the non-absorbed infrared energy with said output element and measuring the intensity of said non-absorbed energy for analysis with subsequent calculation of tissue urea concentration utilizing a multivariate algorithm.

4. The method of claim 3, wherein at least some of said selected wavelengths are from in the range of 4000 $cm^{-1}$ to about 8000 cm$^{-1}$, and wherein said irradiating step and said collecting step are performed using infrared energy within said range.

5. The method of claim 3, further comprising the step of calculating a concentration of said tissue urea concentration in said analyte-containing tissue with said optical apparatus wherein the step of calculating a concentration is done by a multivariate model that was developed by using measured intensities from plural known analyte-containing tissue samples.

6. The method of claim 5, wherein said multivariate model was developed using a partial least squares algorithm to establish the relationship between said measured intensities and known tissue urea concentrations.

7. The method of claim 3, wherein said tissue comprises a skin surface on an underside of a forearm of a patient, and optically coupling said input and output elements to said skin surface.

* * * * *